United States Patent
Evans

(10) Patent No.: US 6,911,467 B2
(45) Date of Patent: Jun. 28, 2005

(54) ANTIDIABETIC AGENTS

(75) Inventor: David Michael Evans, Southampton (GB)

(73) Assignee: Ferring BV, Hoofddorp (NL)

( * ) Notice: Subject to any disclaimer, the term of this patent is extended or adjusted under 35 U.S.C. 154(b) by 331 days.

(21) Appl. No.: 10/129,787

(22) PCT Filed: Nov. 30, 2000

(86) PCT No.: PCT/GB00/04572

§ 371 (c)(1), (2), (4) Date: Jun. 20, 2002

(87) PCT Pub. No.: WO01/40180

PCT Pub. Date: Jun. 7, 2001

(65) Prior Publication Data

US 2003/0096857 A1 May 22, 2003

(30) Foreign Application Priority Data

Nov. 30, 1999 (GB) ................................. 9928330

(51) Int. Cl.$^7$ ........................ A61K 31/40; C07D 207/04
(52) U.S. Cl. ........................ 514/423; 548/530; 548/540
(58) Field of Search ........................ 548/530, 540; 514/423

(56) References Cited

U.S. PATENT DOCUMENTS

| | | | | |
|---|---|---|---|---|
| 5,939,560 A | * | 8/1999 | Jenkins et al. | 548/535 |
| 6,166,063 A | * | 12/2000 | Villhauer | 514/423 |
| 6,172,081 B1 | | 1/2001 | Damon | |
| 6,201,132 B1 | * | 3/2001 | Jenkins et al. | 548/535 |
| 6,319,902 B1 | * | 11/2001 | Sugawara et al. | 514/19 |

FOREIGN PATENT DOCUMENTS

| | | |
|---|---|---|
| WO | WO 95/15309 A | 6/1995 |
| WO | WO 97/40832 A | 11/1997 |
| WO | WO 98/19998 A | 5/1998 |
| WO | WO 00/34241 A | 6/2000 |
| WO | WO 00/55125 A | 9/2000 |
| WO | WO 00/56296 A | 9/2000 |
| WO | WO 00/56297 A | 9/2000 |

OTHER PUBLICATIONS

Thomas E. Hughes et al., "NVP–DPP728 (1–[[[2–[(5–Cyanopyridin–2–yl)amino]ethyl]amino]acetyl]–2–cyan (S)–pyrrolidine), a Slow–Binding Inhibitor of Dipeptidyl Peptidase IV", Biochemistry, 1999, pp. 11597–11603, vol. 38, No. 36, XP000983860.

Takashi Yamada et al., "Studies of Unusual Amino Acids and Their Peptides. VIII The Syntheses of an Iminohexapeptide as a Model of Bottromycin and its Related Iminopeptides", Bull. Chem. Soc. JPN. 1977, pp. 1827–1830, vol. 50, No. 7, XP000983920.

Takashi Yamada et al., "Studies of Unusual Amino Acids and Their Peptides. IX. The Synthetic Study of Bottromycins B1 and B2", Bull. Chem. Soc. JPN. 1978, pp. 878–883, vol. 51, No. 3, XP000983921.

D M Ashworth et al., "2–Cyanopyrrolidides as Potent, Stable Inhibitors of Dipeptidyl Peptidase IV", Bioorganic & Medicinal Chemistry Letters, 1996, pp. 1163–1166, vol. 6, No. 10, XP004124889, Oxford, GB.

* cited by examiner

*Primary Examiner*—Golam M M Shameem
(74) *Attorney, Agent, or Firm*—Foley & Lardner LLP

(57) ABSTRACT

Compounds which are 1-(2'-aminoacyl)-2-cyanopyrrolidine derivatives according to general formula (1) are DP-IV inhibitors for treatment of impaired glucose tolerance or type 2 diabetes; wherein A is selected from groups (2, 3 and 4); X is selected from aminoacyl groups corresponding to the natural amino acids, acyl groups $R^3CO$, groups $R^4COOC(R^5)(R^6)OCO$, methoxycarbonyl, ethoxycarbonyl and benzyloxycarbonyl; $R^1$ is selected from H, $C_1$–$C_6$ alkyl residues, $(CH_2)_aNHW^1$, $(CH_2)_bCOW^2$, $(CH_2)_cOW^3$, $CH(Me)OW^4$, $(CH_2)_d$—$C_6H_4$—$W^5$ and $(CH_2)_eSW^6$, where a is 2–5, b is 1–4, c is 1–2, d is 1–2, e is 1–3, $W^1$ is $COW^6$, $CO_2W^6$ or $SO_2W^6$, $W^2$ is OH, $NH_2$, $OW^6$ or $NHW^6$, $W^3$ is H or $W^6$, $W^4$ is H or $W^6$, $W^5$ is H, OH or OMe, and $W^6$ is $C_1$–$C_6$ alkyl, optionally substituted phenyl, optionally substituted heteroaryl or benzyl and $R^2$ is selected from H and $(CH_2)_n$—$C_5H_3N$—Y, where n is 2–4 and Y is H, F, Cl, $NO_2$ or CN, or $R^1$ and $R^2$ together are —$(CH_2)_p$— where p is 3 or 4; $R^3$ is selected from H, $C_1$–$C_6$ alkyl and phenyl; $R^4$ is selected from H, $C_1$–$C_6$ alkyl, benzyl and optionally substituted phenyl; $R^5$ and $R^6$ are each independently selected from H and $C_1$–$C_6$ alkyl or together are —$(CH_2)_m$—, where m is 4–6; $R^7$ is selected from pyridyl and optionally substituted phenyl; $R^8$ is selected from H and $C_1$–$C_3$ alkyl; and $R^9$ is selected from H, $C_1$–$C_6$ alkyl, $C_1$–$C_6$ alkoxy and phenyl.

23 Claims, No Drawings

ANTIDIABETIC AGENTS

The present invention relates to a series of novel compounds that are useful for the treatment of type 2 diabetes, impaired glucose tolerance and certain other conditions.

BACKGROUND TO THE INVENTION

The enzyme dipeptidyl peptidase IV (EC.3.4.14.5, herein abbreviated as DP-IV, and elsewhere also known as DPP-IV or DAP-IV) is thought to be involved in the regulation of the activities of several hormones. One such hormone is glucagon-like peptide 1 (GLP-1), which is involved in the regulation of post-prandial blood glucose levels, and which is converted from its active form, GLP-1(5–36), to the inactive GLP-1 (7–36) by DP-IV. In cases of type 2 diabetes and impaired glucose tolerance, where hyperglycaemia can lead to tissue damage, it would be advantageous to potentiate the effect of endogenous GLP-1, Accordingly, inhibitors of DP-IV have been proposed as candidate drugs for the treatment of type 2 diabetes and impaired glucose tolerance. For example, Demuth et al. (WO97/40832) disclose the effect of N-isoleucyl-pyrrolidine on blood glucose levels in a relevant animal model. This compound, however, may not be sufficiently potent to be a viable therapeutic agent. More potent inhibitors of DP-IV are disclosed by Jenkins et al. (WO95/15309) and by Villhauer (WO98/19998), but they tend to be unstable and to cyclize in solution. This instability would lead to difficulties in preparing and storing material of adequate quality for human therapeutic use. Therefore, there remains a need for an agent that inhibits DP-IV in vivo, but which is stable enough for commercial manufacture.

BRIEF DESCRIPTION OF THE INVENTION

We have now found a series of derivatives that are chemically stable, but which undergo metabolic activation after administration to a human subject to liberate highly potent inhibitors of DP-IV. In the art, such derivatives are generally termed prodrugs. The compounds of the present invention are useful for the treatment of type 2 diabetes and impaired glucose tolerance, as well as other conditions wherein the potentiation of the action of a hormone normally inactivated by DP-IV gives a therapeutic benefit.

The compounds according to the invention are 1-(2'-aminoacyl)-2-cyanopyrrolidine derivatives according to general formula 1:

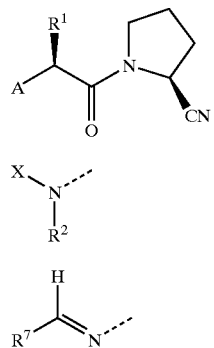

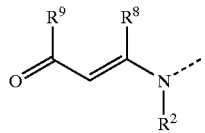

wherein A is selected from groups 2, 3 and 4; X is selected from an aminoacyl group corresponding to one of the natural amino acids, an acyl group $R^3CO$, a group $R^4COOC(R^5)(R^6)OCO$, methoxycarbonyl, ethoxycarbonyl and benzyloxycarbonyl; $R^1$ is selected from H, a $C_1$–$C_6$ alkyl residue, $(CH_2)_aNHW^1$, $(CH_2)_bCOW^2$, $(CH_2)_cOW^3$, $CH(Me)OW^4$, $(CH_2)_d$—$C_6H_4$—$W^5$ and $(CH_2)_eSW^6$, where a is 2–5, b is 1–4, c is 1–2, d is 1–2, e is 1–3, $W^1$ is $COW^6$, $CO_2W^6$ or $SO_2W^6$, $W^2$ is OH, $NH_2$, $OW^6$ or $NHW^6$, $W^3$ is H or $W^6$, $W^4$ is H or $W^6$, $W^5$ is H, OH or OMe, and $W^6$ is $C_1$–$C_6$ alkyl, optionally substituted phenyl, optionally substituted heteroaryl or benzyl and $R^2$ is selected from H and $(CH_2)_n$—$C_5H_3N$—Y, where n is 2–4 and Y is H, F, Cl, $NO_2$ or CN, or $R^1$ and $R^2$ together are —$(CH_2)_p$— where p is 3 or 4; $R^3$ is selected from H, $C_1$–$C_6$ alkyl and phenyl; $R^4$ is selected from H, $C_1$–$C_6$ alkyl, benzyl and optionally substituted phenyl; $R^5$ and $R^6$ are each independently selected from H and $C_1$–$C_6$ alkyl or together are —$(CH_2)_m$—, where m is 4–6; $R^7$ is selected from pyridyl and optionally substituted phenyl; $R^8$ is selected from H and $C_1$–$C_3$ alkyl; and $R^9$ is selected from H, $C_1$–$C_6$ alkyl, $C_1$–$C_6$ alkoxy and phenyl.

The present invention relates to the novel compounds as defined above, to pharmaceutical compositions in which at least one active agent is such a compound, to the use of such compositions for the treatment of certain medical conditions, and to a method of treatment in which the compounds of the invention are administered to a subject in need of treatment.

DETAILED DESCRIPTION OF THE INVENTION

In a first aspect, the present invention comprises a series of novel compounds that are prodrugs of therapeutically useful inhibitors of DP-IV. The compounds of the present invention are 1-(2'-aminoacyl)-2-cyanopyrrolidine derivatives according to general formula 1 below.

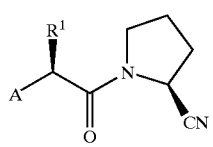

In this general formula, A is a group selected from 2, 3 and 4.

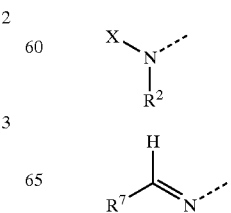

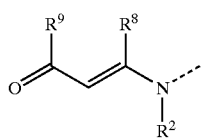

The dashed bond (broken line) indicates the covalent bond that links the nitrogen atom of A to 1.

The group X is an acyl or oxycarbonyl group. Suitable groups are:
(i) amino acyl groups corresponding to one of the natural amino acids alanine (Ala), arginine (Arg), asparigine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val);
(ii) acyl groups $R^3CO$, where $R^3$ is a hydrogen atom, a $C_1$–$C_6$ alkyl group or a phenyl group;
(iii) acyloxymethyleneoxycarbonyl groups $R^4COOC(R^5)(R^6)OCO$, where $R^4$ is a hydrogen atom, a $C_1$–$C_6$ alkyl group, a benzyl group, or a phenyl group which may further be substituted with a $C_1$–$C_3$ group, and $R^5$ and $R^6$ are each independently a hydrogen atom or a $C_1$–$C_6$ alkyl group or $R^5$ and $R^6$ together are a polymethylene unit —$(CH_2)_m$—, where m is an integer of 4–6; and
(iv) methoxycarbonyl, ethoxycarbonyl and benzyloxycarbonyl.

$R^1$ is the side-chain of a naturally occurring amino acid, or an analogue thereof. More specifically, $R^1$ is selected from a hydrogen atom, $C_1$–$C_6$ alkyl residues, $(CH_2)_aNHW^1$, $(CH_2)_bCOW^2$, $(CH_2)_cOW^3$, $CH(Me)OW^4$, $(CH_2)_d$—$C_6H_4$—$W^5$ and $(CH_2)_eSW^6$, where a is an integer of 2–5, b is an integer of 1–4, c is 1 or 2, d is 1 or 2, e is an integer of 1–3, $W^1$ is $COW^6$, $CO_2W^6$ or $SO_2W^6$, $W^2$ is OH, $NH_2$, $OW^6$ or $NHW^6$, $W^3$ is H or $W^6$, $W^4$ is H or $W^6$, $W^5$ is H, OH or OMe, and $W^6$ is $C_1$–$C_6$ alkyl optionally substituted phenyl, optionally substituted heteroaryl or benzyl. Suitable optional substituents on the heteroaryl and phenyl groups include $C_1$–$C_3$ alkyl and $C_1$–$C_3$ alkoxy groups as well as fluorine and chlorine atoms. Up to two such substituents may be present.

$R^2$ is a hydrogen atom or a group —$(CH_2)_nNH$—$C_5H_3N$—Y, where n is an integer of 2–4, $C_5H_3N$ is a divalent pyridyl moiety, and Y is a hydrogen atom, a halogen atom such as a fluorine or chlorine atom, a nitro group or a cyano group.

Alternatively, $R^1$ and $R^2$ together may be —$(CH_2)_p$— where p is 3 or 4.

$R^7$ is selected from pyridyl and optionally substituted phenyl. Suitable optional substituents include $C_1$–$C_3$ alkyl groups, $C_1$–$C_3$ alkoxy groups, halogen atoms, nitro groups, cyano groups and carboxy groups. Up to two such substituents may be present.

$R^8$ is a hydrogen atom or a $C_1$–$C_3$ alkyl group.

$R^9$ is a hydrogen atom, a $C_1$–$C_6$ alkyl group, a $C_1$–$C_6$ alkoxy group or a phenyl group.

In the context of the present disclosure, "alkyl" includes straight-chain and branched alkyl groups as well as cycloalkyl groups. For example, $C_1$–$C_6$ alkyl includes methyl, ethyl, isopropyl, tert-butyl, neopentyl and cyclohexyl groups. Also, "heteroaryl" is intended to include monocyclic five- and six-membered aromatic rings that include from one to three heteroatoms selected from nitrogen, oxygen and sulphur. For example, heteroaryl includes pyrolyl, pyridyl, furyl, thienyl, imidazolyl, thiazolyl, isoxazolyl, thiadiazolyl, pyrimidyl and pyrazinyl.

Certain of the compounds of the present invention have acidic or basic properties and so can exist as salts. Insofar as such salts are non-toxic and otherwise pharmaceutically acceptable, they are included within the scope of the invention. Examples of such salts include, but are not limited to, the acetate, hydrochloride, sulphate, phosphate and benzoate salts of basic compounds, and the sodium, potassium and tetra-alkyl ammonium salts of acidic compounds.

Except when $R^1$ is H, compounds according to general formula 1 have two stereogenic centres (asymmetric carbon atoms), shown below as C*. The stereochemistry at these two positions is preferably the one illustrated. Certain embodiments of $R^1$ and X allow for further stereogenic centres to be introduced, and so the compounds of the invention may exist as epimers, including diastereomers. All such optical isomers, including mixtures of such optical isomers, are considered to be within the scope of the invention.

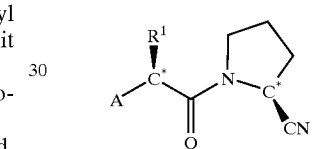

In a preferred embodiment, the present invention comprises a compound according to general formula 1 in which $R^1$ is other than H and $R^2$, where present, is H. In a more preferred embodiment, $R^1$ is $C_1$–$C_6$ alkyl.

In another preferred embodiment, the present invention comprises a compound according to general formula 1 in which $R^1$ is H and A is selected from groups according to general formulae 2 and 4 with $R^2$ being —$(CH_2)_nNH$—$C_5H_3N$—Y. In a more preferred embodiment n is 2 and Y is CN. In a most preferred embodiment, the NH group is at the 2-position and the CN group is at the 5-position of the pyridine ring.

In another preferred embodiment, the present invention comprises a compound according to general formula 1 in which A is a group according to general formula 2 and X is an amino acyl group. In one more preferred embodiment, X is an amino acyl group corresponding to a basic amino acid such as lysine or arginine, and most preferably arginine. In another more preferred embodiment, X is an amino acyl group corresponding to glycine.

In another preferred embodiment, the present invention comprises a compound according to general formula 1 in which A is a group according to general formula 2 and X is a group $R^4COOC(R^5)(R^6)OCO$. In one more preferred embodiment, $R^4$ is $C_1$–$C_6$ alkyl. In another more preferred embodiment, one of $R^5$ and $R^6$ is H and the other is methyl. Most preferably, $R^4$ and one of $R^5$ and $R^6$ are methyl and the other of $R^5$ and $R^6$ is H.

In another preferred embodiment, the present invention comprises a compound according to general formula 1 in which A is a group according to general formula 2 and X is a methoxycarbonyl group.

In another preferred embodiment, the present invention comprises a compound according to general formula 1 in which A is a group according to general formula 3.

In another preferred embodiment, the present invention comprises a compound according to general formula 1 in which A is a group according to general formula 4. In a more preferred embodiment $R^8$ is $C_1$–$C_3$ alkyl, and most preferably it is methyl. In another more preferred embodiment, $R^9$ is $C_1$–$C_3$ alkyl or $C_1$–$C_3$ alkoxy, and most preferably it is methyl or methoxy.

Compounds that incorporate the features of more than one of these preferred embodiments are particularly preferred. A most preferred embodiment of the present invention is a compound selected from:

(2S)-1-((2'S)-2'-(1"-acetoxyethoxycarbonylamino)-3',3'-dimethylbutanoyl)-pyrrolidine-2-carbonitrile;

(2S)-1-(N'-(1"-acetoxyethoxycarbonyl)isoleucyl)pyrrolidine-2-carbonitrile;

(2S)-1-(N'-(methoxycarbonyl)isoleucyl)pyrrolidine-2-carbonitrile;

(2S)-1-((N')-(4"-oxopent-2"-en-2"-yl)isoleucyl)pyrrolidine-2-carbonitrile;

(2S)-1-(glycylisoleucyl)pyrrolidine-2-carbonitrile;

(2S)-1-(arginylisoleucyl)pyrrolidine-2-carbonitrile;

(2S)-1-((2'S)-2'-(acetoxymethoxycarbonylamino)-3',3'-dimethylbutanoyl)-pyrrolidine-2-carbonitrile;

(2S)-1-((2'S)-2'-(1"-acetoxyethoxycarbonylamino)-2'-cyclohexylacetyl)-pyrrolidine-2-carbonitrile;

(2S)-1-((2'S)-2'-(1"-acetoxyethoxycarbonylamino)-4',4'-dimethylpentanoyl)-pyrrolidine-2-carbonitrile;

(2S)-1-(N'-(1"-acetoxyethoxycarbonyl)-O'-tert-butylserinyl)pyrrolidine-2-carbonitrile;

(2S)-1-($N^\alpha$-(1'-acetoxyethoxycarbonyl)-$N^\omega$-p-toluenesulphonyllysinyl)-pyrrolidine-2-carbonitrile;

(2S)-1-(N-(1'-acetoxyethoxycarbonyl)-N-(2"-(5'"-cyanopyridin-2'"-ylamino)-ethyl)glycinyl)pyrrolidine-2-carbonitrile;

(2S)-1-(N'-(benzyloxycarbonyl)-O'_tert-butylthreoninyl)pyrrolidine-2-carbonitrile;

(2S)-1-(S'-tert-butyl-N'-(ethyloxycarbonyl)cysteinyl)pyrrolidine-2-carbonitrile;

(2S)-1-($N^\omega$-acetyl-$N^\alpha$-benzoyllysinyl)pyrrolidine-2-carbonitrile; and (2S)-1-($N^\alpha$-(acetyl)-$N^\omega$-(benzyloxycarbonyl)ornithinyl)pyrrolidine-2-carbonitrile The compounds according to the present invention can be prepared by standard techniques that are well known in the field of organic chemistry. In many cases, a suitable starting material is an amine according to general formula 5, in which $R^1$ and $R^2$ have the same meaning as defined previously.

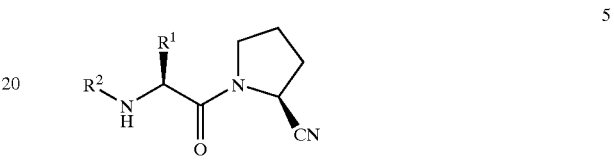

5

The synthesis of such compounds is described in, for example, Jenkins et al. (WO95/15309), Villhauer (WO98/19998), Ashworth et al. (Bioorg. Med. Chem. Lett. 1996, 6(10), 1163–66) and Li et al. (Arch. Biochem. Biophys. 1995, 323(1), 148–54). Compounds not explicitly described in these publications can be made by routine modification of the methods given therein. The steps involved in the preparation of the compounds of the invention from compounds according to general formula 5 depend on the nature of the group A.

(i) A=

X=amino acyl group.

Scheme 1

Scheme 1 illustrates the preparation of these compounds in two steps. Chn represents the side chain of an amino acid. Depending on the amino acid being used, Chn may be H (for glycine), $CH_3$ (alanine), $(CH_3)_2CH$ (valine), $(CH_3)_2CHCH_2$ (leucine), $CH_3CH_2CH(CH_3)$ (isoleucine), $C_6H_5CH_2$ (phenylalanine), $HOC_6H_4CH_2$ (tyrosine), $C_8H_6NCH_2$ (tryptophan), $HOOCCH_2$ (aspartic acid), $HOOCCH_2CH_2$ (glutamic acid), $H_2NOCCH_2$ (asparagine), $H_2NOCCH_2CH_2$ (glutamine), $HOCH_2$ (serine), $CH_3CH(OH)$ (threonine), $HSCH_2$ (cysteine), $CH_3SCH_2CH_2$ (methionine), $C_3H_3N_2CH_2$ (histidine), $H_2N(CH_2)_4$ (lysine) and $H_2NC(:NH)(CH_2)_3$ (arginine). As will be understood by those familiar with the practice of peptide chemistry, several of these side chains contain functional groups that are reactive under the conditions necessary to effect the condensation of the two fragments. These functional groups must be protected with an appropriate masking group. Such groups are described in, for example, "Protective Groups in Organic Synthesis", T. W. Greene, Wiley-Interscience, 1981. Chn* therefor represents the same side chains but with any necessary protecting groups.

Similarly, PG represents a protecting group for an amino function.

The 1-(2'-aminoacyl)-2-cyanopyrrolidine 5 can be condensed with the appropriately protected amino acid 6 to give intermediate 7 using a variety of conditions that are well known in the field of peptide chemistry. Generally, the two components are dissolved in an appropriate solvent, which is normally an aprotic solvent such as dichloromethane or dimethylformamide or a mixture of these, and the solution is cooled to 0° C. or below. One or two equivalents of an amine base such as diisopropylethylamine or dimethylaminopyridine may be added to the solution. A condensing agent is then added and the mixture is stirred until the starting materials have been consumed, as indicated by, for example, analytical thin layer chromatography. If the reaction is slow, it may be advisable to allow the mixture to warm up to ambient temperature to accelerate the process. Suitable condensing agents include DCC (dicyclohexylcarbodiimide), BOP ((benzotriazol-1-yloxy)-tris(dimethylamino)phosphonium hexafluorophosphate), PyBOP® ((benzotriazol-1-yloxy)tripyrrolidinophosphonium hexafluorophosphate), PyBroP® (bromo-tripyrrolidinophosphonium hexafluorophosphate) and HBTU (O-(benzotriazol-1-yl)-N,N,N',N'-tetramethyluronium hexafluorophosphate).

Deprotection of intermediate 7 gives the target compound $1^A$ (i.e. a compound of general formula 1 with A according to general formula 2 and X an amino acyl residue).

Suitably protected proline may be used instead of 6 to give the analogous compound with X being a prolyl residue. All the protected amino acids are items of commerce.

(ii) A=

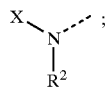

$X=R^3CO$.

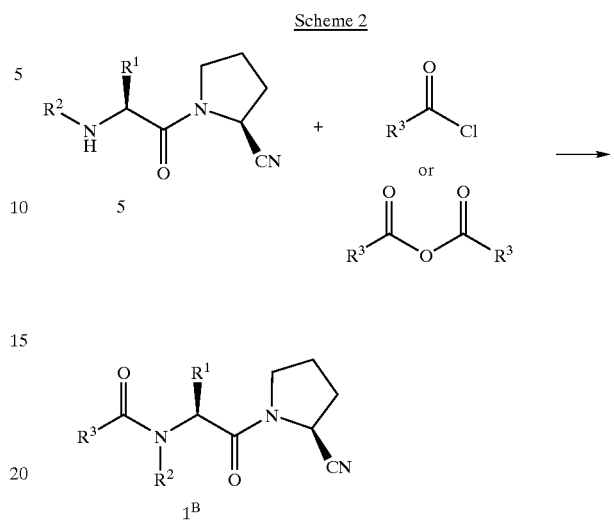

Scheme 2 illustrates the preparation of these compounds. The starting material 5 is treated with an acyl chloride or an anhydride in an aprotic solvent and in the presence of an amine base such as described above, to give the product $1^B$. When $R^3=H$ it is not possible to use the acyl chloride or anhydride. In this case a mixed anhydride is used. The reagent can conveniently be prepared from formic acid and acetic anhydride.

(iii) A=

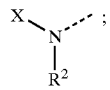

$X=R^4COOC(R5)(R6)OCO$.

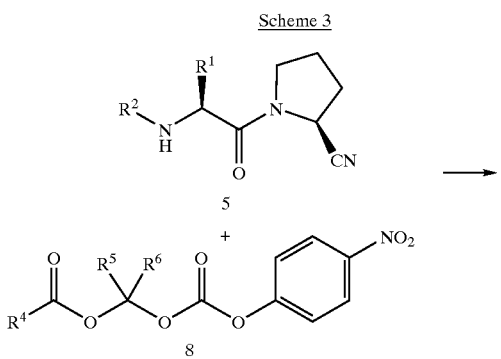

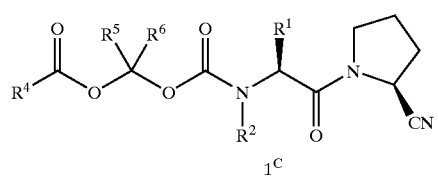

Scheme 3 illustrates the preparation of these compounds. The starting material 5 is treated with a p-nitrophenyl carbonate 8 in an aprotic solvent and in the presence of an amine base such as described previously to give the product $1^c$. The carbonate is prepared according to the method described by Alexander et al., J. Med. Chem.31, 318, 1988.

(iv) A=

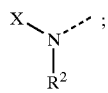

X=methoxycarbonyl, ethoxycarbonyl, benzyloxycarbonyl.

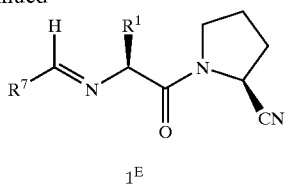

$1^E$

Scheme 5 illustrates the preparation of these compounds. The starting material $5^A$ (i.e. a compound according to general formula 5 with $R^2$=H) is reacted with an aldehyde 9 in the presence of an acidic catalyst such as, for example, p-toluenesulphonic acid. The reaction is performed in a Scheme 4

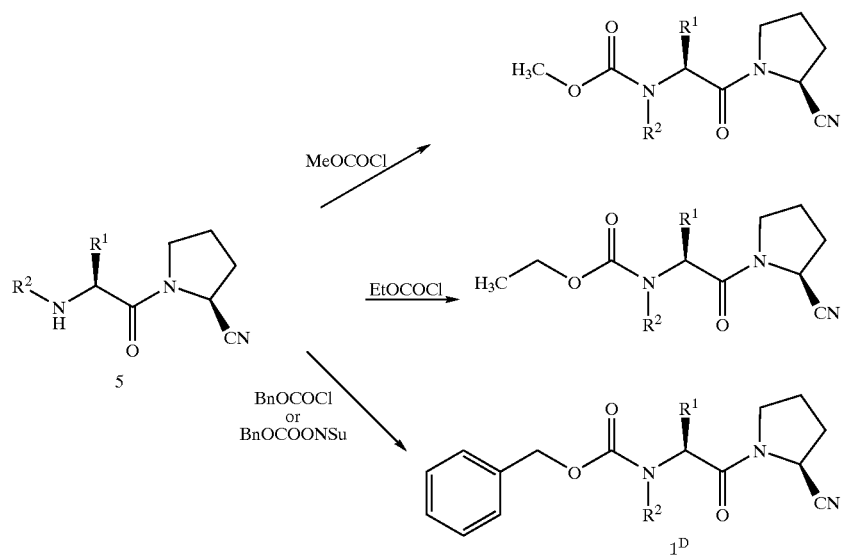

Scheme 4 illustrates the preparation of these compounds. The starting material 5 is treated with a chloroformate in an aprotic solvent and in the presence of an amine base such as described previously to give the product $1^D$. Since benzyl chloroformate (BnOCOCl) is not very stable, it may conveniently be replaced by benzyl 1-succinimidyl carbonate (BnOCONSu). This and all the chloroformates are items of commerce.

(v) A=

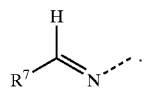

solvent such as cyclohexane or toluene at an elevated temperature such as at the boiling point of the solvent. Water is removed continuously, either by azeotropic distillation or with a desiccating agent such as activated molecular sieves.

The aldehydes 9 are items of commerce.

(vi) A=

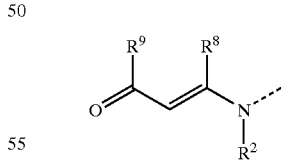

Scheme 5

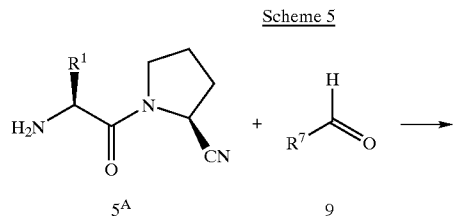

Scheme 6

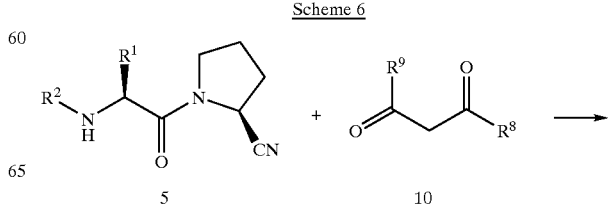

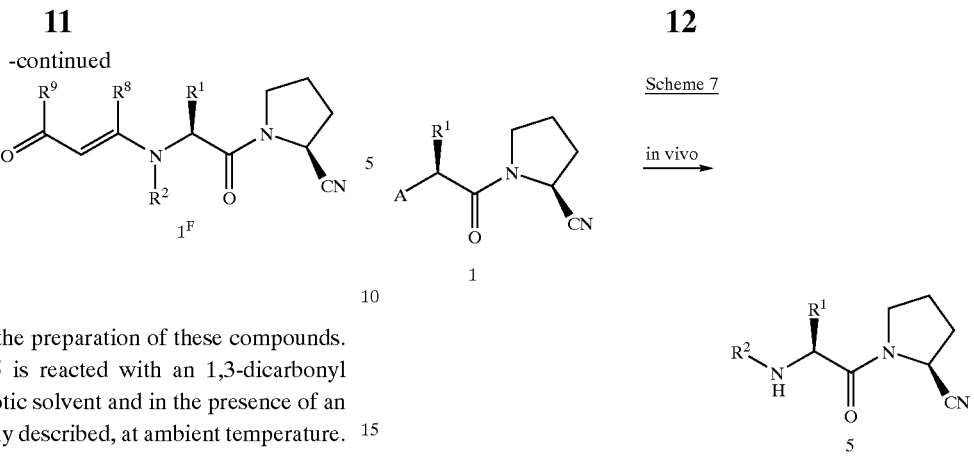

Scheme 6 illustrates the preparation of these compounds. The starting material 5 is reacted with an 1,3-dicarbonyl compound 10 in an aprotic solvent and in the presence of an amine base, as previously described, at ambient temperature.

The dicarbonyl compounds 10 are either items of commerce or may be prepared according to well-established procedures.

Other synthetic routes are, of course, possible. In general, they differ from those described above in the order in which steps are performed. Two examples are illustrated in Scheme 7.

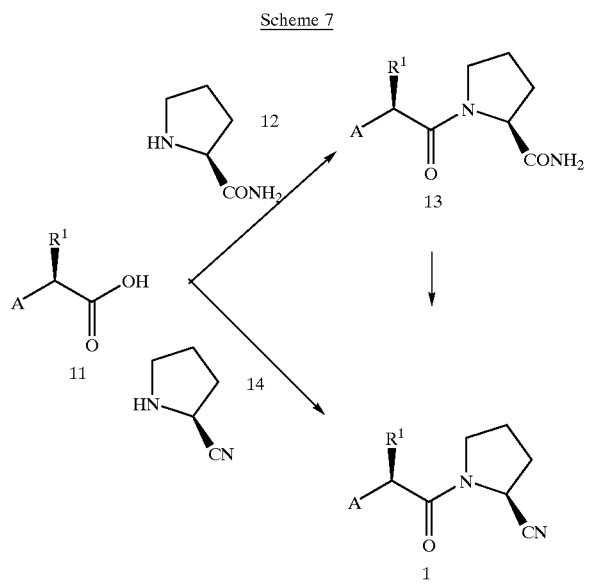

Scheme 7

Intermediate 11 is prepared according to the methods previously described. It can be condensed with prolineamide (12) according to the methods described in Scheme 1 to give the intermediate 13. This can be dehydrated by treatment with trifluoroacetic anhydride to give the target compound. Alternatively, intermediate 11 can be condensed with pro-linenitrile (14) to give the target compounds directly.

Compounds according to general formula 1 (the compounds of the present invention) are metabolised in the body to give compounds according to general formula 5. These metabolites are inhibitors of DP-IV.

As discussed previously, inhibitors of DP-IV are believed to be useful in the treatment of certain medical conditions. Accordingly, the compounds of the present invention are useful in the treatment of these same medical conditions. In particular, the compounds of the present invention are useful in the treatment of impaired glucose tolerance and type 2 diabetes. They can also be useful in the treatment of reproductive disorders such as infertility due to polycystic ovary syndrome. A further use is in the treatment of growth hormone insufficiency leading to small stature. Other medical conditions are also included within the scope of the invention.

For use in the treatment of these disorders, the compounds of the invention will generally be included in a pharmaceutical composition and formulated appropriately for the intended route of administration. Such compositions comprise a second aspect to the present invention. The pharmaceutical composition may include other such pharmaceutically acceptable excipients as are generally known in the art, such as bulking agents, diluents, dispersants, preservatives, colouring and flavouring agents and the like. The choice of the excipients will depend on the manner in which the composition is to be formulated and administered. The composition may be administered by the routes generally known in the art. For example, the composition may be formulated as a tablet, capsule, syrup or powder for oral administration, as a lozenge or wafer for sub-lingual or buccal administration, as a suppository for rectal or vaginal administration, as a solution, suspension or powder for nasal administration, as a cream or lotion for topical administration, as a patch for transdermal administration, or as a solution or suspension for subcutaneous, intramuscular or intravenous injection. Injectable forms may include encapsulated and other controlled-release formulations as are known in the art to be suitable for depot administration. A preferred composition is a tablet for oral administration.

In a third aspect, the invention comprises a method of treatment of glucose intolerance or type 2 diabetes wherein a person in need of such treatment is administered a therapeutically effective amount of a compound as described above. The dosing regimen will generally be decided by the treating physician, taking into account the particular characteristics of the patient. The dose will typically be from 1 mg to 500 mg once per day or up to four times per day.

The foregoing general description is further illustrated below in a number of examples. These are intended to demonstrate the implementation of the invention, but they do not in any way limit the scope of what has been described hereto.

EXAMPLES

Solvents and reagents were generally used as supplied without further purification. The structures of all intermediates were confirmed by ¹H NMR. Final products were further characterised by mass spectroscopy and/or elemental analysis.

Example 1

(2S)-1-((2'S)-2'-(1"-Acetoxyethoxycarbonylamino)-3',3'-dimethyl-butanoyl)pyrrolidine-2-carbonitrile

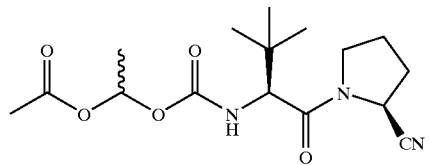

A solution of (2S)-1-((2'S)-2'-amino-3',3'-dimethylbutanoyl)pyrrolidine-2-carbonitrile hydrochloride (180 mg, 0.73 mmol; prepared according to Jenkins et al., WO95/15309), α-acetoxyethyl p-nitrophenyl carbonate (220 mg, 0.82 mmol; prepared according to Alexander et al., J. Med. Chem. 31, 318, 1988) and triethylamine (90 mg, 0.90 mmol) in dichloromethane (25 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (eluant EtOAc:Pet. Ether 60–80° C.; 3:7) yielding a white solid identified as the title compound (170 mg, 0.50 mmol, 68%).

MS:—ESI {M+H}⁺=340.2 ¹H NMR (CDCl₃): δ 1.02, 1.03 (9H, 2×s), 1.42–1.46 (3H, m), 2.03, 2.05 (3H, 2×s), 2.15–2.25 (4H, m), 3.69–3.76 (2H, m), 4.23–4.28 (1H, m), 4.77–4.79 (1H, m), 5.43 (1H, d, J=9.5 Hz), 6.73–6.77 (1H, m) ppm

Example 2

(2S)-1-(N'-(1"-Acetoxyethoxycarbonyl)isoleucyl)pyrrolidine-2-carbonitrile

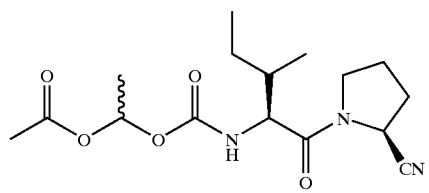

A solution of (2S)-1-(isoleucyl)pyrrolidine-2-carbonitrile hydrochloride (500 mg, 2.04 mmol; prepared according to Jenkins et al., WO95/15309), α-acetoxyethyl p-nitrophenyl carbonate (610 mg, 2.27 mmol; prepared according to Alexander et al., J. Med. Chem. 31, 318, 1988) and triethy-lamine (250 mg, 2.50 mmol) in dichloromethane (40 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (eluant EtOAc:Pet. Ether 60–80° C.; 3:7) yielding a colourless oil identified as the title compound (480 mg, 1.42 mmol, 70%).

MS:—ESI {M+H}⁺=340.0 ¹H NMR (CDCl₃): δ 0.86–0.89 (6H, m), 0.92–0.97 (1H, m), 1.41–1.45 (3H, m), 150–1.80 (2H, m), 2.02 (3H, d, J=5.2 Hz), 2.14–2.27 (4H, m), 3.60–3.75 (2H, m), 4.23–4.26 (1H, t, J=7.6 Hz), 4.77 (1H, d, J=2.3 Hz), 5.30–5.50 (1H, m), 6.73–6.77 (1H, m) ppm

Example 3

(2S)-1-(N'-(Methoxycarbonyl)isoleucyl)pyrrolidine-2-carbonitrile

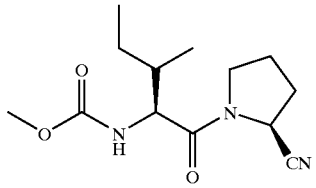

A solution of (2S)-1-(isoleucyl)pyrrolidine-2-carbonitrile hydrochloride (300 mg, 1.22 mmol; prepared according to Jenkins et al., WO95/15309), methyl chloroformate (125 mg, 1.3 mmol) and triethylamine (150 mg, 1.50 mmol) in dichloromethane (40 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (EtOAc:Pet. Ether 60–80° C.; 4:6) yielding a colourless oil identified as the title compound (310 mg, 1.16 mmol, 95%).

MS:—ESI {M+H}⁺=268.2 ¹H NMR (CDCl₃): δ 0.85–0.95 (6H, m), 1.10–1.25 (1H, m), 1.54–1.77 (2H, m), 2.11–2.26 (4H, m), 3.62 (3H, s), 3.66–3.79 (2H, m), 4.21 (1H, t, J=9.2 Hz), 4.74–4.78 (1H, m), 5.30 (1H, d, J=9.1 Hz) ppm.

Example 4

(2S)-1-((N')-(4"-Oxopent-2"en-2"-yl)isoleucyl)pyrrolidine-2-carbonitrile

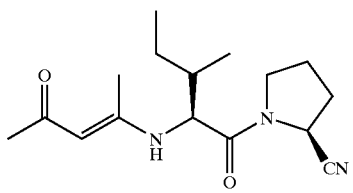

A solution of (2S)-1-(isoleucyl)pyrrolidine-2-carbonitrile hydrochloride (150 mg, 0.61 mmol; prepared according to Jenkins et al., WO95/15309), 2,4-pentanedione (68 mg, 0.68 mmol) and triethylamine (75 mg, 0.75 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant EtOAc-:Pet. Ether 60–80° C.; 7:3) yielding a colourless oil identified as the title compound (85 mg, 0.29 mmol, 47%).

MS:—ESI {M+H}$^+$=292.3 $^1$H NMR (CDCl$_3$): δ 0.87–0.98 (6H, m), 1.19–1.25 (1H, m), 1.61–1.69 (2H, m), 1.84 (3H, s), 1.98 (3H, s), 2.15–2.25 (4H, m), 3.49–3.54 (1H, m), 3.62–3.69 (1H, m), 3.95–3.98 (1H, m), 4.75–4.79 (1H, m), 4.98 (1H, s), 11.09 (1H, d, J=8.1 Hz) ppm Example 5

(2S)-1-(Glycylisoleucyl)pyrrolidine-2-carbonitrile

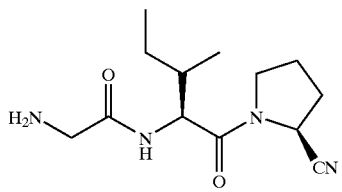

(a) (2S)-1-(Isoleucyl)pyrrolidine-2-carbonitrile

To a solution of Boc-isoleucine hemihydrate (0.96 g, 4 mmol) and PyBOP® (2.34 g, 4.5 mmol) in dichloromethane (25 ml) was added DIPEA (1.74 ml, 10 mmol). To that solution was added solid (S)-pyrrolidine-2-carbonitrile hydrochloride (0.60 g, 4.5 mmol) followed by another portion of DIPEA (697 μl, 4 mmol). The reaction mixture was stirred for 2 h. The solvent was removed by rotary evaporation, and the residue was taken up in ethyl acetate. The resulting solution was washed with 0.3M sodium bisulfate (2×), saturated sodium bicarbonate (2×), water and saturated sodium chloride. The organic phase was dried with anhydrous sodium sulfate and the solvent was removed by rotary evaporation. The residue was dissolved in a mixture of TFA (95%) and water (5%). After 1 h most of TFA and water was removed under reduced pressure, and the residue was triturated with ether, resulting in the formation of a precipitate. The precipitate was collected and dried in vacuo to give the trifluoroacetate salt of the title product as a white solid; yield 0.58 g (1.8 mmol, 45%).

(b) (2S)-1-(Glycylisoleucyl)pyrrolidine-2-carbonitrile

To a solution of Boc-glycine (0.21 g, 1.2 mmol) and PyBOP® (0.62 g, 1.2 mmol) in dichloromethane (3 ml) was added DIPEA (522 μl, 3 mmol). To that solution was added the product of Example 5a (0.28 g, 0.9 mmol) followed by another portion of DIPEA (157 μl, 0.9 mmol). The reaction mixture was stirred overnight. The solvent was removed by rotary evaporation and the residue was taken up in ethyl acetate. The resulting solution was washed with 0.3M sodium bisulfate (2×), saturated sodium bicarbonate (2×), water and saturated sodium chloride. The organic phase was dried with anhydrous sodium sulfate and the solvent was removed by rotary evaporation. The residue was dissolved in a mixture of TFA (95%) and water (5%) and the mixture was stirred overnight. Most of TFA and water was removed under reduced pressure. The residue was subjected to purification by reverse-phase HPLC to give the trifluoroacetate salt of the final product as a white powder; yield 171 mg (50%).

Example 6

(2S)-1-(Arginylisoleucyl)pyrrolidine-2-carbonitrile

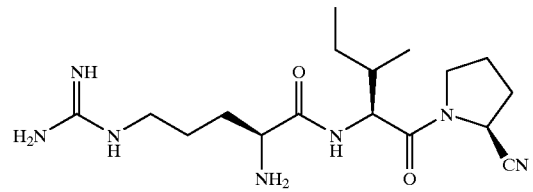

To a solution of Boc-Arg(Mtr)-OH (0.58 g, 1.2 mmol) and PyBOP® (0.62 g, 1.2 mmol) in dichloromethane (3 ml) was added DIPEA (522 μl, 3 mmol). To that solution was added the product of Example 5a (0.28 g, 0.9 mmol) followed by another portion of DIPEA (157 μl, 0.9 mmol). The reaction mixture was stirred overnight. The solvent was removed by rotary evaporation, and the residue was taken up in ethyl acetate. The resulting solution was washed with 0.3M sodium bisulfate (2×), saturated sodium bicarbonate (2×), water and saturated sodium chloride. The organic phase was dried with anhydrous sodium sulfate and the solvent was removed by rotary evaporation. The residue was dissolved in a mixture of TFA (95%) and water (5%) and the mixture was stirred overnight. Most of TFA and water was removed under reduced pressure and the residue was triturated with ether. The ethereal layer was decanted off, and the residue was subjected to purification by reverse-phase HPLC to give the trifluoroacetate salt of the final product as a white powder; yield 83 mg (19%).

Example 7

(2S)-1-((2'S)-2'-(Acetoxymethoxycarbonylamino)-3', 3'-dimethyl-butanoyl)pyrrolidine-2-carbonitrile

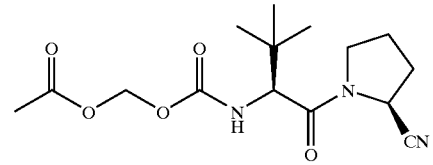

A solution of (2S)-1-((2'S)-2'-amino-3',3'-dimethylbutanoyl)pyrrolidine-2-carbonitrile hydrochloride (150 mg, 0.61 mmol; prepared according to Jenkins et al., WO95/15309), acetoxymethyl p-nitrophenyl carbonate (168 mg, 0.66 mmol; prepared according to Alexander et al., J. Med. Chem. 31, 318, 1988) and triethylamine (70 mg, 0.70 mmol) in dichloromethane (25 ml). was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant EtOAc:Pet. Ether 60–80° C.; 4:6) yielding a white solid identified as the title compound (188 mg, 0.58 mmol, 95%).

MS:—ESI {M+H}⁺=326.1 ¹H NMR (CDCl₃): δ 1.03 (9H, s), 2.09 (3H, s), 2.16–2.24 (4H, m), 3.72–3.77 (2H, m), 4.25 (1H, d, J=9.6 Hz), 4.77–4.80 (1H, m), 5.68 (1H, d), 5.68 (2H, s) ppm Example 8

(2S)-1-((2'S)-2'-(1"-Acetoxyethoxycarbonylamino)-2'-cyclohexylacetyl)pyrrolidine-2-carbonitrile

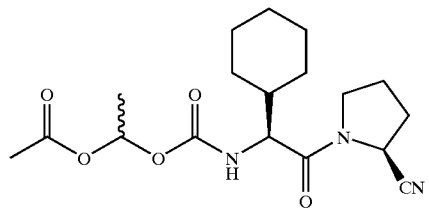

A solution of (2S)-1-((2'S)-2'-amino-2'-cyclohexylacetyl)pyrrolidine-2-carbonitrile trifluoroacetate (100 mg, 0.28 mmol; prepared according to Jenkins et al., WO95/15309), α-acetoxyethyl p-nitrophenyl carbonate (76 mg, 0.29 mmol; prepared according to Alexander et al., J. Med. Chem. 31, 318, 1988) and triethylamine (35 mg, 0.35 mmol) in dichloromethane (25 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (eluant EtOAc-:Pet. Ether 60–80° C.; 4:6) yielding a white solid identified as the title compound (43 mg, 0.12 mmol, 41%).

MS:—ESI {M+H}⁺=366.2 ¹H NMR (CDCl₃): δ 0.97–1.21 (4H, m), 1.40–1.48 (3H, m), 1.67–1.77 (7H, m), 2.02 (3H, d, J=7.8 Hz), 2.11–2.26 (4H, m), 3.65–3.73 (2H, m), 4.16–4.22 (1H, m), 4.76 (1H, d, J=4.2 Hz), 5.36–5.41 (1H, m), 6.73–6.77 (1H, m) ppm Example 9

(2S)-1-((2'S)-2'-(1"-Acetoxyethoxycarbonylamino) 4',4'-dimethyl-pentanoyl)pyrrolidine-2-carbonitrile

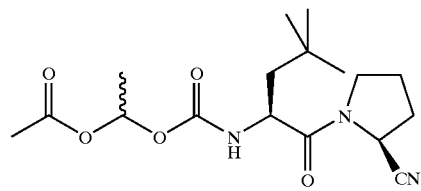

A solution of (2S)-1-((2'S)-2'-amino-4',4'-dimethylpentanoyl)pyrrolidine-2-carbonitrile trifluoroacetate (100 mg, 0.30 mmol; prepared according to Jenkins et al., WO95/15309), α-acetoxyethyl p-nitrophenyl carbonate (87 mg, 0.33 mmol; prepared according to Alexander et al., J. Med. Chem. 31, 318, 1988) and triethylamine (40 mg, 0.40 mmol) in dichloromethane (25 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (eluant EtOAc:Pet. Ether 60–80° C.; 4:6) yielding a white solid identified as the title compound (32 mg, 0.09 mmol, 31%).

MS:—ESI {M+H}⁺=354.2 ¹H NMR (CDCl₃): δ 0.97, 0.98 (9H, 2×s), 1.41–1.43 (3H, m), 1.44–1.62 (2H, m), 2.03 (3H, d, J=2.3 Hz), 2.16–2.21 (4H, m), 3.61–3.63 (1H, m), 3.74–3.78 (1H, m), 4.45–4.52 (1H, m), 4.75–4.77 (1H, m), 5.24–5.29 (1H, m), 6.73–6.78 (1H, m) ppm Example 10

(2S)-1-(N'-(1"-Acetoxyethoxycarbonyl)-O'-tert-butylserinyl)-pyrrolidine-2-carbonitrile

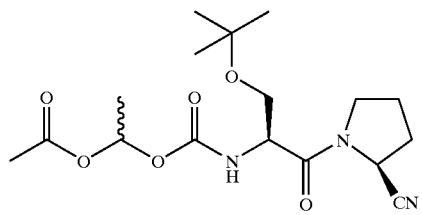

A solution of (2S)-1-(O'-tert-butylserinyl)pyrrolidine-2-carbonitrile hydrochloride (30 mg, 0.11 mmol; prepared according to Jenkins et al., WO95/15309), α-acetoxyethyl p-nitrophenyl carbonate (32 mg, 0.12 mmol; prepared according to Alexander et al., J. Med. Chem. 31, 318, 1988) and triethylamine (20 mg, 0.20 mmol) in dichloromethane (25 ml) was stirred at room temperature for 18 hours. After this time the solvent was removed in vacuo and the residue was taken up in ethyl acetate (70 ml). This solution was washed with 0.3M KHSO₄, sat. NaHCO₃, water and brine, dried (Na₂SO₄) and evaporated. The residue was purified by flash chromatography (eluant EtOAc:Pet. Ether 60–80° C.; 4:6) yielding a white solid identified as the title compound (14 mg, 0.038 mmol, 35%).

MS:—ESI {M+H}⁺=370.1 ¹H NMR (CDCl₃): δ 1.11–1.15 (9H, m), 1.41–1.45 (3H, m), 2.04 (3H, d, J=4.9 Hz), 2.10–2.15 (2H, m), 3.43–3.62 (5H, m), 3.90–4.00 (1H, m), 4.50–4.65 (1H, m), 4.73 (1H, d, J=5.2 Hz), 5.45–5.72 (1H, m), 6.76–6.79 (1H, m) ppm

Example 11

(2S)-1-(N''-(1'-Acetoxyethoxycarbonyl)-N''-p-toluenesulphonyllysinyl)pyrrolidine-2-carbonitrile

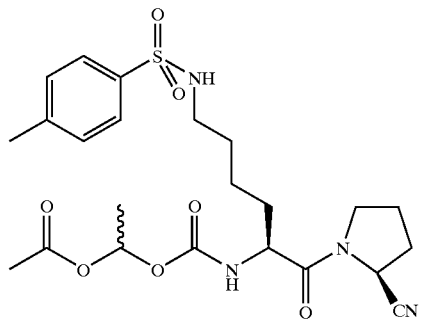

A solution of (2S)-1-(N''-p-toluenesulphonyllysinyl) pyrrolidine-2-carbonitrile trifluoroacetate (100 mg, 0.20 mmol; prepared according to Jenkins et al., WO95/15309), α-acetoxyethyl p-nitrophenyl carbonate (61 mg, 0.23 mmol; prepared according to Alexander et al., J. Med. Chem. 31, 318, 1988) and triethylamine (30 mg, 0.30 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant EtOAc:Pet. Ether 60–80° C.; 7:3) yielding a white solid identified as the title compound (51 mg, 0.10 mmol, 49%).

MS:—ESI {M+H}$^+$=509.0 $^1$H NMR (CDCl$_3$): δ 1.41–1.48 (6H, m), 1.51–1.69 (2H, m), 2.05 (3H, d, J=18.3 Hz), 2.12–2.28 (5H, m), 2.41 (3H, s), 2.86–2.93 (2H, m), 3.63–3.64 (2H, m), 4.38–4.42 (1H, m), 4.72–4.73 (1H, m), 4.74–4.79, 5.10–5.20 (1H, 2×m), 5.54–5.62 (1H, m), 6.74–6.79 (1H, m), 7.29 (2H, d, J=7.7 Hz), 7.71 (2H, d, J=8.4 Hz) ppm

Example 12

(2S)-1-(N-(1'-Acetoxyethoxycarbonyl)-N-(2''-(5'''-cyanopyridin-2'''-ylamino)ethyl)glycinyl) pyrrolidine-2-carbonitrile

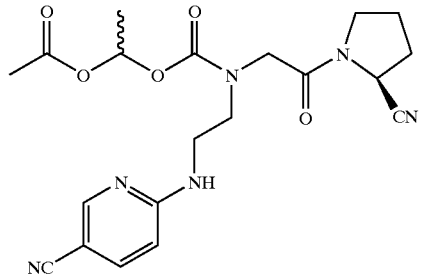

A solution of 1-([2-[(5-cyanopyridin-2-yl)amino]ethyl]amino]acetyl)-2-cyano-(S)-pyrrolidine bis(trifluoroacetate) (100 mg, 0.19 mmol; prepared according to Villhauer et al., WO98/19998), α-acetoxyethyl p-nitrophenyl carbonate (56 mg, 0.21 mmol; prepared according to Alexander et al., J. Med. Chem. 31, 318, 1988) and triethylamine (50 mg, 0.50 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant EtOAc:Pet. Ether 60–80° C.; 9:1) yielding a white solid identified as the title compound (13 mg, 0.03 mmol, 16%).

MS:—ESI {M+H}$^+$=429.2 $^1$H NMR (CDCl$_3$): δ 1.21–1.32 (3H, m), 1.40–1.46 (1H, m),1.99–2.05 (4H, m), 2.17–2.31 (4H, m), 3.50–3.63 (6H, m), 4.40–4.50 (1H, m), 4.77 (1H, d, J=5.9 Hz), 6.45–6.49 (1H, m), 6.68–6.77 (1H, m), 7.44–7.48 (1H, m), 8.32 (1H, s) ppm

Example 13

(2S)-1-(N'-(Benzyloxycarbonyl)-O'—tert-butylthreoninyl)-pyrrolidine-2-carbonitrile

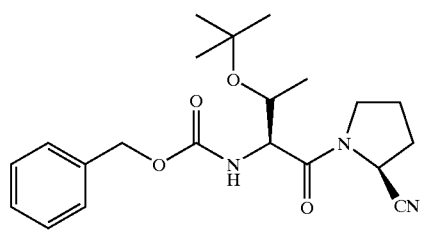

A solution of (2S)-1-(O'-tert-butylthreoninyl)pyrrolidine-2-carbonitrile hydrochloride (35 mg, 0.12 mmol; prepared according to Jenkins et al., WO95/15309), benzyl chloroformate (32 mg, 0.13 mmol) and triethylamine (24 mg, 0.24 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant: chloroform: methanol; 98:2) yielding a white solid identified as the title compound (47 mg, 0.12 mmol, 100%).

MS:—ESI {M+H}$^+$=388.3 $^1$H NMR (CDCl$_3$): δ 1.10–1.30 (3H, m), 1.18 (9H, s), 2.00–2.45 (4H, m), 3.55–3.70 (1H, m), 3.85–4.00 (2H, m), 4.30–4.40 (1H, m), 4.70–4.80 (1H, m), 5.07 (2H, s), 5.75 (1H, d, J=8.15 Hz), 7.20–7.45 (5H, m) ppm

Example 14

(2S)-1-(S'-tert-Butyl-N'-(ethyloxycarbonyl)cysteinyl)pyrrolidine-2-carbonitrile

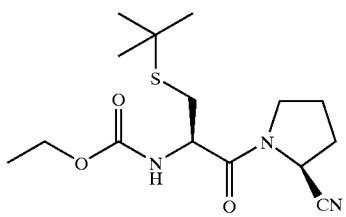

A solution of (2S)-1-(S'-tert-butylcysteinyl)pyrrolidine-2-carbonitrile trifluoroacetate (1000 mg, 0.27 mmol; prepared according to Jenkins et al., WO95/15309), ethylchloroformate (35 mg, 0.32 mmol) and triethylamine (50 mg, 0.50 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant EtOAc:Pet. Ether 60–80° C.; 8:2) yielding a white solid identified as the title compound (30 mg, 0.092 mmol, 35%).

MS:—ESI $\{M+H\}^+$=328.1 $^1$H NMR (CDCl$_3$): δ 1.18 (3H, t, J=7 Hz), 1.30 (9H, s), 2.17–2.24 (4H, br m), 2.82–2.85 (2H, m), 3.70–3.82 (2H, br m), 4.05–4.09 (2H, m), 4.48–4.53 (1H, m), 4.74–4.77 (1H, m), 5.41–5.44 (1H, m) ppm.

Example 15

(2S)-1-N"-Acetyl-N"-benzoyllysinyl)pyrralidine-2-carbonitrile

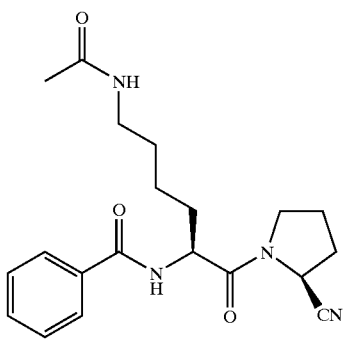

A solution of (2S)-1-(N"-acetyllysinyl)pyrrolidine-2-carbonitrile trifluoroacetate (100 mg, 0.22 mmol; prepared according to Jenkins et al., WO95/15309), benzoyl chloride (343 mg, 0.24 mmol) and triethylamine (45 mg, 0.45 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant chloroform: methanol; 97:3) yielding a white solid identified as the title compound (83 mg, 0.22 mmol, 100%).

MS:—ESI $\{M+H\}^+$=387.6 $^1$H NMR (CDCl$_3$): δ 1.56–1.78 (4H, br m), 1.94 (3H, s), 2.12–2.20 (4H, br m), 3.21–3.23 (2H, m), 3.59–3.72 (2H, m), 4.65–4.69 (2H, m), 5.07 (2H, s), 5.18–5.21 (1H, m), 6.69–6.72 (1 H, m), 7.24–7.34 (5H, m) ppm

Example 16

(2S)-1-(N"-(Acetyl)-N"-(benzyloxycarbonyl)ornithinyl)-pyrrolidine-2-carbonitrile

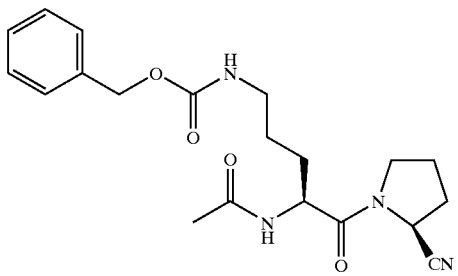

A solution of (2S)-1-(N"-(benzyloxycarbonyl)ornithinyl)pyrrolidine-2-carbonitrile trifluoroacetate (100 mg, 0.23 mmol; prepared according to Jenkins et al., WO95/15309), acetyl chloride (20 mg, 0.26 mmol) and triethylamine (50 mg, 0.50 mmol) in dichloromethane (25 ml) was stirred at room temperature for 18 hours. After this time the solvent was removed in vacuo and the residue was taken up in ethyl acetate (70 ml). This solution was washed with 0.3M KHSO$_4$, sat. NaHCO$_3$, water and brine, dried (Na$_2$SO$_4$) and evaporated. The residue was purified by flash chromatography (eluant chloroform: methanol; 97:3) yielding a white solid identified as the title compound (49 mg, 0.13 mmol, 55%).

MS:—ESI $\{M+H\}^+$=371.2 $^1$H NMR (CDCl$_3$): δ 1.30–1.65 (4H, m), 1.75–1.95 (2H, m), 1.90 (3H, s), 2.10–2.40 (4H, m), 3.10–3.30 (2H, m), 3.65–3.90 (2H, m), 4.70–4.90 (2H, m), 5.90–6.00 (1H, m), 7.30–7.50 (4H, m), 7.70–7.80 (2H, m) ppm

Example 17

In Vitro Inhibitory Activity vs. DP-IV

The compounds of the previous examples were assayed as inhibitors of DP-IV according to the method described in Ashworth et al. (Bioorg. Med. Chem. Lett. 1996, 6(10), 1163–66). No significant inhibitory activity was detected up to 10 μM, indicating that the prodrugs of the invention are at least 1000 times less potent than the active inhibitors from which they are derived. Hence it can be assumed that any in vivo activity seen is due to bioconversion into the parent inhibitors.

Example 18

In Vivo Activity in Glucose Tolerance Model

The activity of the compounds was investigated in male Zucker Fatty Rats between 10 and 20 weeks of age. The animals were fasted overnight and then administered with the test compound (10 mg/kg) as a solution by oral gavage.

One hour later hour a blood sample (200 µl) is taken from the tail vein to establish a baseline (t=0) glucose level, then the animals are given glucose (1 g/kg as a 40% wt/vol solution) orally. Further blood samples are taken at t=10, 20, 30, 60 and 120 minutes. Glucose is determined by an enzymatic assay. Typical results are given in the Table below.

|  | Blood glucose (mg/dl); mean ± SE, n = 4 | | | | | |
| --- | --- | --- | --- | --- | --- | --- |
| Compound | t = 0 | t = 10 | t = 20 | t = 30 | t = 60 | t = 120 |
| vehicle | 95.1 ± 7.36 | 151.6 ± 8.12 | 164.3 ± 10.7 | 153.2 ± 7.8 | 153.4 ± 7.8 | 122.4 ± 7.0 |
| Example 2 | 80.2 ± 4.2 | 122.2 ± 7.8 | 117.8 ± 4.8 | 104.4 ± 5.6 | 117.6 ± 6.7 | 111.3 ± 12.1 |
| Example 3 | 86.4 ± 3.4 | 175.1 ± 3.8 | 148.5 ± 23.2 | 136.7 ± 16.9 | 120.6 ± 8.3 | 101.9 ± 4.5 |
| Example 5 | 80.5 ± 1.4 | 141.3 ± 14.5 | 134.2 ± 10.3 | 129.2 ± 8.2 | 114.6 ± 8.1 | 121.2 ± 5.8 |
| Reference | 91.4 ± 5.2 | 125.8 ± 8.9 | 110.0 ± 21.5 | 110.9 ± 4.4 | 112.2 ± 7.5 | 108.7 ± 8.9 |

The reference compound in the above experiments was the compound of Example 11 of WO95/15309. This is the parent compound from which the prodrugs of Examples 2–6 of the present disclosure are derived.

It is clear from the above results that the prodrugs are effective at reducing hyperglycaemia after the glucose challenge, but that they are not always as effective as the reference compound at early time points. This is what would be expected for prodrugs that are converted in high yield to the parent drug. The results at early time points are a result of the need for metabolic conversion of the circulating prodrug.

In a separate experiment the test compound was given at the same dose (10 mg/kg) but 12 hours before the oral glucose challenge. The results are given below.

|  | Blood glucose (mg/dl); mean ± SE, n = 4 | | | | | | |
| --- | --- | --- | --- | --- | --- | --- | --- |
| Compound | t = 0 | t = 10 | t = 20 | t = 30 | t = 60 | t = 120 | AUC |
| vehicle | 84.2 ± 3.7 | 145.5 ± 6.6 | 134.3 ± 8.0 | 127.2 ± 10.1 | 122.9 ± 8.7 | 112.2 ± 8.6 | 4556 ± 458 |
| Example 1 | 83.7 ± 3.8 | 113.5 ± 10.8 | 111.3 ± 9.9 | 91.9 ± 11.8 | 99.3 ± 10.0 | 116.9 ± 14.4 | 2430 ± 591 |

The AUC (area under the concentration-time curve) is greatly reduced, showing that the prodrug enables significant antihyperglycaemic activity to be maintained for 12 hours.

The above results illustrate that the compounds of the present invention exhibit antihyperglycaemic activity after oral administration in a relevant animal model of glucose intolerance. Hence it is to be expected that they would be effective in the treatment of human impaired glucose tolerance and type 2 diabetes. Furthermore, the in vivo results confirm that the prodrugs are converted to active DP-IV inhibitors in the circulation, and that they could be used in the treatment of all the other pathologies for which such inhibitors have been proposed as therapeutic agents.

Example 19

Pharmaceutical Formulations

19A—50 mg Tablets

Tablets containing 50 mg of the compound of Example 1 are prepared from the following:

| Compound of Example | 154.5 g |
| --- | --- |
| Corn Starch | 53.5 g |
| Hydroxypropylcellulose | 13.5 g |
| Carboxymethylcellulose calcium | 11.0 g |
| Magnesium stearate | 2.0 g |
| Lactose | 165.5 g |
| Total | 400.0 g |

The materials are blended and then pressed to give 2000 tablets of 200 mg, each containing 50 mg of the compound of Example 1.

The compounds of Examples 2, 3 and 5 were formulated separately into respective tablets in the same manner. The compounds of Examples 4 and 6 to 16 were similarly formulated separately into tablets containing 100 mg of the respective compounds.

19B—100 mg Suppository

Suppositories containing 100 mg of the compound of Example 2 are prepared from the following:

| Compound of Example 2 | 154.5 g |
| --- | --- |
| Corn Starch | 210.0 g |
| Colloidal silica | 2.5 g |
| Povidone 30 | 49.0 g |
| Magnesium stearate | 23.0 g |
| Adipic acid | 57.0 g |
| Sodium bicarbonate | 43.0 g |

-continued

| Sodium lauryl sulphate | 5.0 g |
| --- | --- |
| Lactose | 456.0 g |
| Total | 1000.0 g |

The materials are blended and then pressed to give suppositories of 1 g. each containing 100 mg of compound of Example 2. The compounds of Examples 1, 3 to 5 and 6 to 16 were formulated into respective suppositories in the same manner.

What is claimed is:

1. A compound according to the general formula 1, or a pharmaceutically acceptable salt thereof,

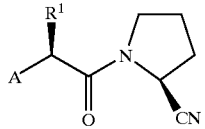

wherein A is

and $R^1$ is selected from H, $C_1$–$C_6$ alkyl, $(CH_2)_a NHW^1$, $(CH_2)_b COW^2$, $(CH_2)_c OW^3$, $CH(Me)OW^4$, $(CH_2)_d$—$C_6H_4$—$W^5$, and $(CH_2)_e SW^6$, where a is 2–5, b is 1–4, c is 1–2, d is 1–2, e is 1–3; $W^1$ is $COW^6$, $CO_2W^6$, or $SO_2W^6$; $W^2$ is OH, $NH_2$, $OW^6$, or $NHW^6$; $W^3$ is H or $W^6$; $W^4$ is H or $W^6$; $W^5$ is H, OH, or OMe; and $W^6$ is $C_1$–$C_6$ alkyl, benzyl, optionally substituted phenyl, or optionally substituted heteroaryl, where the optional substituents are one or two groups selected from $C_1$–$C_3$ alkyl, $C_1$–$C_3$ alkoxy, F, and Cl;

$R^2$ is H or —$(CH_2)_n NH$—$C_5H_3N$—Y, where n is 2–4 and Y is selected from H, F, Cl, $NO_2$, and CN, or $R^1$ and $R^2$ together are —$(CH_2)p$-, where p is 3 or 4;

X is selected from
(i) L-alpha-amino acyl groups selected from Ala, Arg, Asn, Asp, Cys, Gln, Glu, Gly, His, Ile, Leu, Lys, Met, Phe, Pro, Ser, Thr, Trp, and Tyr;
(ii) groups $R^3CO$, where $R^3$ is H, $C_1$–$C_6$ alkyl, or phenyl;
(iii) groups $R^4COOC(R^5)(R^6)OCO$, where $R^4$ is H, $C_1$–$C_6$ alkyl, benzyl, or optionally substituted phenyl which may include up to two substituent groups selected from $C_1$–$C_3$ alkyl, $C_1$–$C_3$ alkoxy, F, and Cl; and $R^5$ and $R^6$ are independently H or $C_1$–$C_6$ alkyl, or $R^5$ and $R^6$ together are —$(CH_2)_m$— where m is an integer of 4–6; and
(iv) methoxycarbonyl, ethoxycarbonyl, and benzyloxycarbonyl groups.

2. A compound according to claim 1, wherein $C_1$–$C_6$ alkyl includes straight chain, branched, and cyclo-alkyl.

3. A compound according to claim 1, wherein $R^1$ is other than H and $R^2$ is H.

4. A compound according to claim 3, wherein $R^1$ is $C_1$–$C_6$ alkyl.

5. A compound according to claim 1, wherein $R^1$ is H and $R^2$ is —$(CH_2)_n NH$—$C_5H_3N$—Y.

6. A compound according to claim 5, wherein n is 2 and Y is CN.

7. A compound according to claim 6, wherein the NH substituent is at the 2-position and the cyano group is at the 5-position of the pyridyl ring.

8. A compound according to claim 1, wherein X is an L-alpha-amino acyl group selected from Ala, Arg, Asn, Asp, Cys, Gn, Glu, Gly, His, Ile, Leu, Lys, Met, Phe, Pro, Ser, Thr, Trp, and Tyr.

9. A compound according to claim 8, wherein the L-alpha-amino acyl group is a lysyl or argininyl group.

10. A compound according to claim 9, wherein the L-alpha-amino acyl group is an argininyl group.

11. A compound according to claim 1, wherein the L-alpha-amino acyl group is a glycinyl group.

12. A compound according to claim 1, wherein X is $R^4COOC(R^5)(R^6)OCO$.

13. A compound according to claim 12, wherein $R^4$ is $C_1$–$C_6$ alkyl.

14. A compound according to claim 12, wherein one of $R^5$ and $R^6$ is H and the other is methyl.

15. A compound according to claim 12, wherein $R^4$ is methyl; one of $R^5$ and $R^6$ is H and the other is methyl.

16. A compound according to claim 1, wherein X is methoxycarbonyl.

17. A compound according to claim 1, wherein the compound is selected from (2S)-1-((2'S)-2'-(1"-acetoxyethoxycarbonylamino)-3',3'-dimethylbutanoyl)-pyrrolidine-2-carbonitrile;

(2S)-1-(N'-(1"-acetoxyethoxycarbonyl)isoleucyl)pyrrolidine-2-carbonitrile;

(2S)-1-(N'-(methoxycarbonyl)isoleucyl)pyrrolidine-2-carbonitrile;

(2S)-1-((N')-(4"oxopent-2"-en-2"-yl)isoleucyl)pyrrolidine-2-carbonitrile;

(2S)-1-(glycylisoleucyl)pyrrolidine-2-carbonitrile;

(2S)-1-(arginylisoleucyl)pyrrolidine-2-carbonitrile;

(2S)-1-((2'S)-2'-(acetoxymethoxycarbonylamino)-3',3'-dimethylbutanoyl)-pyrrolidine-2-carbonitrile;

(2S)-1-((2'S)-2'-(1"-acetoxyethoxycarbonylamino)-2'-cyclohexylacetyl)-pyrrolidine-2-carbonitrile;

(2S)-1-((2'S)-2'-(1"-acetoxyethoxycarbonylamino)4',4'-dimethylpentanoyl)-pyrrolidine-2-carbonitrile;

(2S)-1-(N'-(1"-acetoxyethoxycarbonyl)-O"-tert-butylserinyl)pyrrolidine-2-carbonitrile;

(2S)-1-(N$^\alpha$-(1'-acetoxyethoxycarbonyl)-N$^\omega$-p-toluenesulphonyllysynyl)-pyrrolidine-2-carbonitrile;

(2S)-1-(N-(1'-acetoxyethoxycarbonyl)-N-(2"-(5'"-cyanopyridin-2'"-ylamino)-ethyl)glycinyl)pyrrolidine-2-carbonitrile (2S)-1-(N'-(benzyloxycarbonyl)-O'-tert-butylthreoninyl)pyrrolidine-2-carbonitrile;

(2S)-1-(S'-tert-butyl-N'-(ethyloxycarbonyl)cysteinyl)pyrrolidine-2-carbonitrile;

(2S)-1-(N$^\omega$-acetyl-N$^\alpha$-benzoyllysynyl)pyrrolidine; and (2S)-1-(N$^\alpha$-(acetyl)-N$^\omega$-(benzyloxycarbonyl)omithinyl)pyrrolidine)-2-carbonitrile.

18. At least one compound selected from optical isomers of compounds according to claim 1.

19. At least one compound selected from pharmaceutically acceptable salts of compounds according to claim 1.

20. A pharmaceutical composition comprising a compound according to claim 1.

21. The pharmaceutical composition of claim 20, wherein the composition is formulated to be administered as a treatment for impaired glucose tolerance or type 2 diabetes.

22. A pharmaceutical composition comprising a compound according to the general formula 1, or a salt thereof,

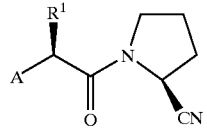

1 wherein A is

and $R^1$ is selected from H, $C_1$–$C_6$ alkyl, $(CH_2)_a NHW^1$, $(CH_2)_b COW^2$, $(CH_2)_c OW^3$, $CH(Me)OW^4$, $(CH_2)_d$—$C_6H_4$—$W^5$, and $(CH_2)_e SW^6$, where a is 2–5, b is 1–4, c is 1–2, d is 1–2, e is 1–3; $W^1$ is $COW^6$, $CO_2W^6$, or $SO_2W^6$; $W^2$ is OH, $NH_2$, $OW^6$, or $NHW^6$; $W^3$ is H or $W^6$; $W^4$ is H or $W^6$; $W^5$ is H, OH, or OMe; and $W^6$ is $C_1$–$C_6$ alkyl, benzyl, optionally substituted phenyl, or optionally substituted heteroaryl, where the optional substituents are one or two groups selected from $C_1$–$C_3$ alkyl, $C_1$–$C_3$ alkoxy, F, and Cl;

$R^2$ is H or —$(CH_2)_n NH$—$C_5H_3N$—Y, where n is 2–4 and Y is selected from H, F, Cl, $NO_2$, and CN, or $R^1$ and $R^2$ together are —$(CH_2)p$—, where p is 3 or 4;

X is selected from
  (i) L-alpha-amino acyl groups selected from Ala, Arg, Asn, Asp, Cys, Gln, Glu, Gly, His, Ile, Leu, Lys, Met, Phe, Pro, Ser, Thr, Trp, Tyr, and Val;
  (ii) groups $R^3CO$, where $R^3$ is H, $C_1$–$C_6$ alkyl, or phenyl;
  (iii) groups $R^4COOC(R^5)(R^6)OCO$, where $R^4$ is H, $C_1$–$C_6$ alkyl, benzyl, or optionally substituted phenyl which may include up to two substituent groups selected from $C_1$–$C_3$ alkyl, $C_1$–$C_3$ alkoxy, F, and Cl; and $R^5$ and $R^6$ are independently H or $C_1$–$C_6$ alkyl, or $R^5$ and $R^6$ together are —$(CH_2)_m$— where m is an integer of 4–6; and
  (iv) methoxycarbonyl, ethoxycarbonyl, and benzyloxycarbonyl groups.

23. A method of treating impaired glucose tolerance or type 2 diabetes which comprises administering to a person in need thereof a therapeutically effective amount of a pharmaceutical composition according to claim 22.

* * * * *